United States Patent [19]

Sitta

[11] Patent Number: 5,412,823
[45] Date of Patent: May 9, 1995

[54] PATIENT'S EXAMINATION TABLE FOR CARRYING OUT MEDICAL EXAMINATIONS

[75] Inventor: Stefano Sitta, Sasso Marconi, Italy

[73] Assignee: C.A.T. di Corsini Guiseppe & C. S.P.A., Bologna, Italy

[21] Appl. No.: 201,164

[22] Filed: Feb. 22, 1994

[30] Foreign Application Priority Data

Feb. 26, 1993 [IT] Italy ................ BO93A0070

[51] Int. Cl.⁶ .............................. A61G 13/00
[52] U.S. Cl. .............................. 5/601; 5/610; 5/611; 378/209
[58] Field of Search .......... 5/601, 610, 611, 11; 378/209

[56] References Cited

U.S. PATENT DOCUMENTS

| | | | |
|---|---|---|---|
| 3,302,022 | 1/1967 | Brenner et al. | 5/601 X |
| 3,396,274 | 8/1968 | Hogan | 5/601 |
| 4,912,754 | 3/1990 | Van Steenburg | 378/209 |
| 5,013,018 | 5/1991 | Sicek et al. | 5/601 |
| 5,131,105 | 7/1992 | Harrowood et al. | 5/611 X |
| 5,156,166 | 10/1992 | Sebring | 5/611 X |

*Primary Examiner*—Michael F. Trettel
*Attorney, Agent, or Firm*—Dvorak and Traub

[57] ABSTRACT

The patient examination table for medical examinations comprises a support structure, a patient rest plane, first movement means to rotate the patient rest plane in two directions about a horizontal axis, potentially covering an angular range of not less than 180 degrees, and a second movement means to translate the patient rest surface vertically in both directions. (FIG. 1).

9 Claims, 4 Drawing Sheets

PATIENT'S EXAMINATION TABLE FOR CARRYING OUT MEDICAL EXAMINATIONS

BACKGROUND OF THE INVENTION.

The present invention relates to an examination table which can be varied in height and angle for use in the performing of various medical examinations, especially radiological examinations such as stratigraphy, mammography, tomography, or endoscopic examinations, where wide-ranging patient position changes are needed in order to carry out all of the examinations correctly.

Prior art examination tables relating to the above field are equipped with blocking elements to constrain the supine patient to the table, and are inferiorly solid to a slide element having a horizontal-axis part-cylindrical shape, with the arched portion inferiorly arranged. This slide element is inferiorly supported and can perform oscillations about its own axis on command of special movement means which bring the patient into all the positions necessary for the examinations, starting from a vertical position with head up to a slightly inclined position with respect to a horizontal plane, with the patient's head slightly below his feet. Owing to well-known geometrical problems, a so-conformed slide element together with its support elements cannot bring the patient into a position where his head is considerably below the level of his feet, nor, obviously, where the patient is in a vertical head-down position. Numerous examinations would be more efficiently carried out if the above-described positions were possible.

Further, height regulation of the known examination tables is not possible, which once again leads to drawbacks where numerous types of medical tests are concerned.

SUMMARY OF THE INVENTION.

The principal aim of the present invention is thus to eliminate the above-mentioned drawbacks, by providing an independent examination table whereon the patient's position can be simply changed and whereon the patient can be moved throughout a range of positions between a vertical one with head up and a vertical one with head down, i.e. 90 degrees in either direction with reference to a horizontal plane.

The invention, as it is characterised in the claims, solves the above-mentioned problems by providing an examination table for patients suitable for various medical examinations, comprising a support structure, a plane for the patient to lie on connected to the support structure, and first movement means to set the patient rest plane in motion about a horizontal axis; further comprising guide means supporting the patient surface, which guide means can move the patient rest plane in two vertical senses, and second movement means to cause the patient rest plane to translate along the guide means.

In a preferred embodiment of the invention, the movement means comprise at least one screw-coupling device consisting of a bar-screw and a nut. The screw-coupling device is connected to the patient rest plane, and second bi-directional motor means are provided to turn both screw and nut.

Further, the first movement means preferably comprise support means of the patient surface, to rotate the patient surface in two directions about its horizontal axis, covering an angular range preferably of 180 degrees, but increasable even up to 270 degrees.

One of the advantages afforded by the invention is that it is simple and relatively cheap to manufacture.

BRIEF DESCRIPTION OF THE DRAWINGS

The technical characteristics of the invention are contained in the claims that follow, and its advantages will better emerge from the detailed description that follows, made with reference to the accompanying figures, which represent a purely non-limiting preferred embodiment, and in which:

DESCRIPTION OF THE PREFERRED EMBODIMENTS

Figure 1:
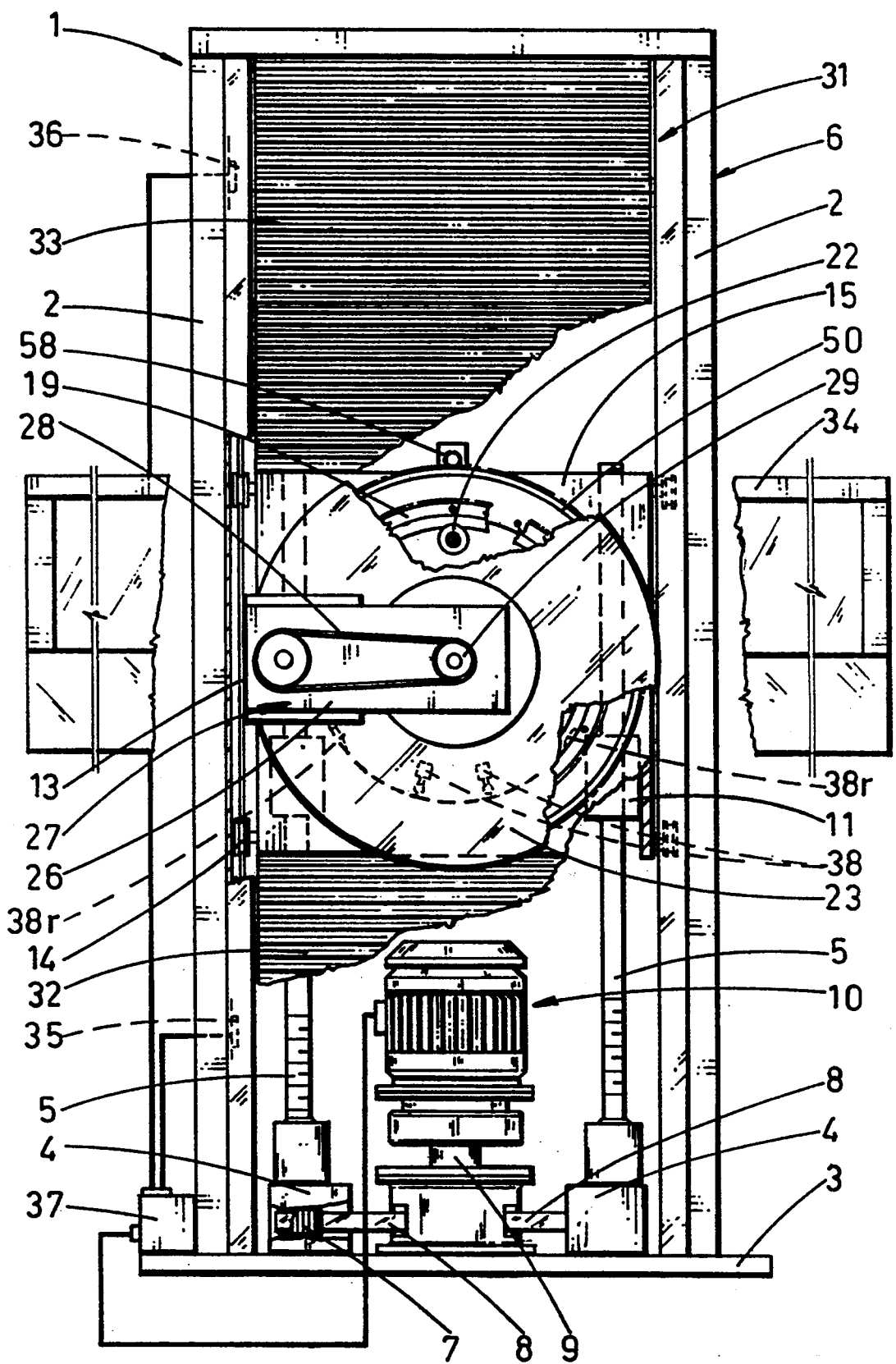
FIG. 1 shows a schematic frontal view, partially in section and with some parts removed better to evidence others, of an examination table according to the invention.

With reference to the figures, 1 denotes an examination table 1 for use in carrying out medical examinations and in general for diagnostic testing. In the latter activity, naturally, the patient will be kept still while the tests are carried out, since the instrument and equipment-bearing structure, in effect no other than the present examination table 1 adapted for a different purpose, will be moving about the patient's body. In the following description the table will be referred to as an examination table 1, but the range of protection sought extends to an instrument and equipment-bearing structure as above.

The examination table 1 comprises a support structure, namely a column 2 with its lower end resting on the ground. A horizontal base wall 3 rotatably supports the lower ends of two screw elements by means of support elements 4 connected to it. The two screw elements are each constituted by a vertical threaded bar 5 housed inside a parallelepiped case 6 encasing the column 2. The upper ends of the threaded bars 5 are rotatably supported (not illustrated) by respective support elements (not illustrated) similar to the support elements 4 and solid to respective upper portions of the case 6.

Figure 2:
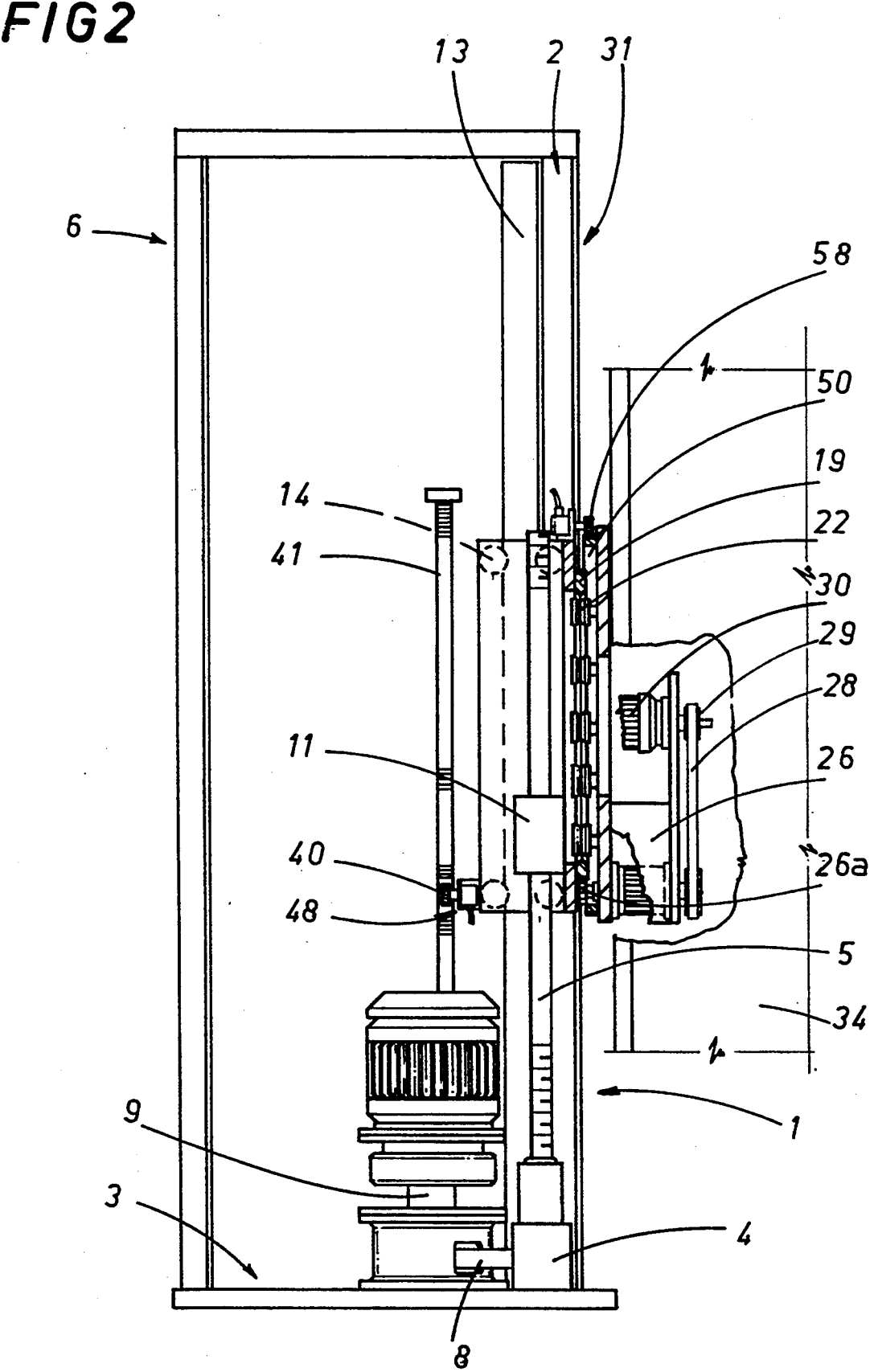
FIG. 2 shows a schematic partially-sectioned lateral view, of the examination table of FIG. 1.

Each of the threaded bars 5 has a cogwheel 7 keyed on to its lower end (only one of the cogwheels 7 is illustrated in FIG. 1): a cogbelt 8 winds around the cogwheels 7 and around another cogwheel (not illustrated) keyed on a vertical drive shaft 9 of a bi-directional gear reducer 10 supported on the wall 3. A nut 11 is keyed on each of the threaded bars 5 (see also FIGS. 2 and 4), and each of the two nuts 11 supports a rectangular wall 12 developing in a vertical direction and arranged such that the two walls 12 are parallel to each other and opposite, and so that the threaded bars 5 are housed in the space between the two walls 12. On the other side to the side adjacent to a threaded bar 5, each of the walls 12 is close to a guide element constituted by a vertical and rectangular wall 13 which is part of or solid to the column 2 and parallel to the wall 12. The wall 13 is narrower than the wall 12.

Figure 4:
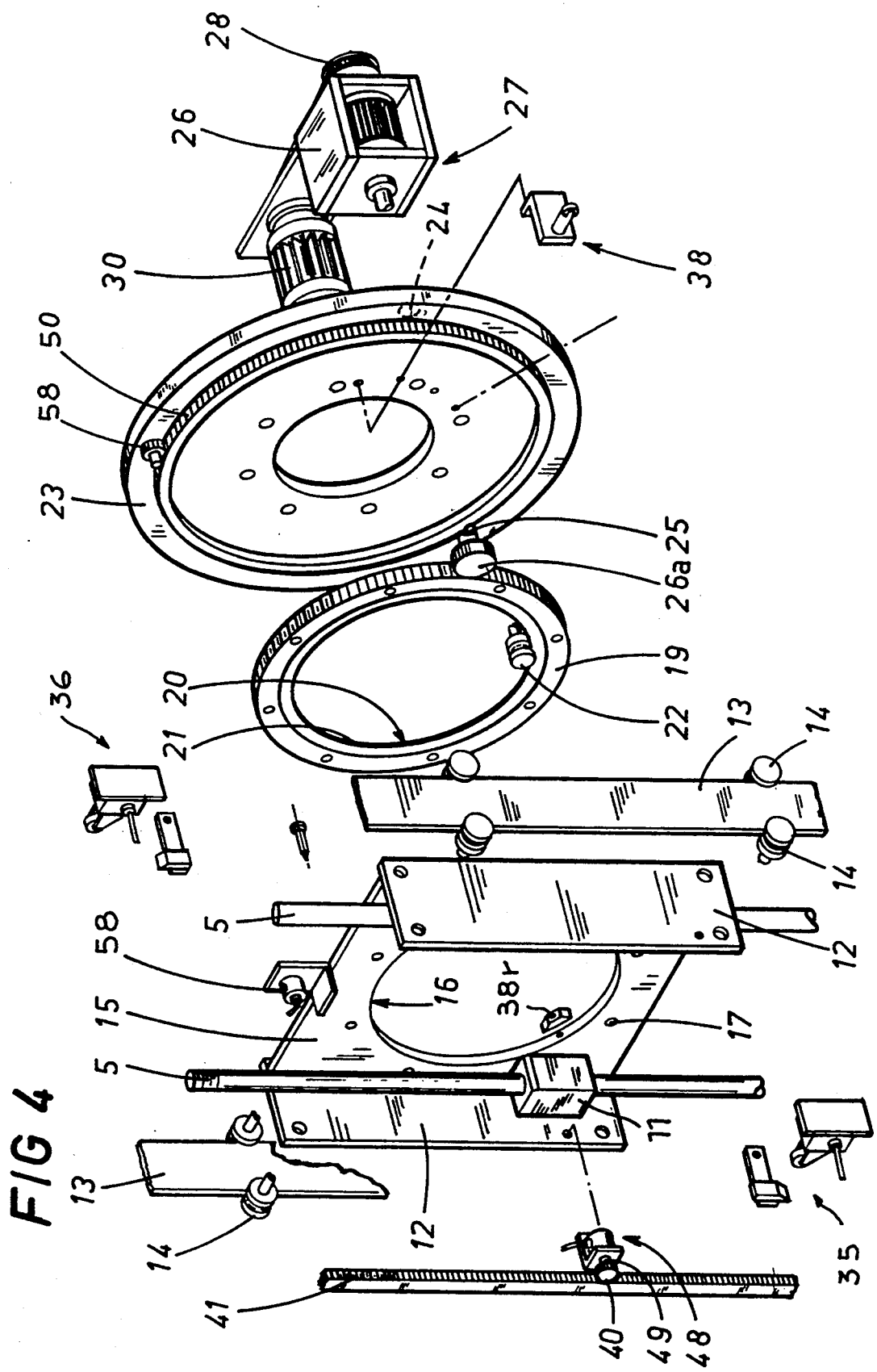
FIG. 4 shows a perspective exploded view of a part of the table of the previous figures.

Each of the two vertical edges of the walls 13 is breasted by a vertically-aligned idle roller pair 14 having horizontal axes normal to the walls 12 and 13. These rollers 14 are supported on the wall 12. The walls 12 are reciprocally connected, at respective vertical edges lying on a vertical plane parallel to the lie plane of the axes of the threaded bars 5, by a square frontal wall 15 (FIG. 4). At its center the wall 15 has a horizontal-axis (X) circular aperture 16, at the edge of which aperture 16 the wall 15 is crossed by a plurality of horizontal threaded holes 17 (FIG. 4) normal to the wall 15.

Figure 3:
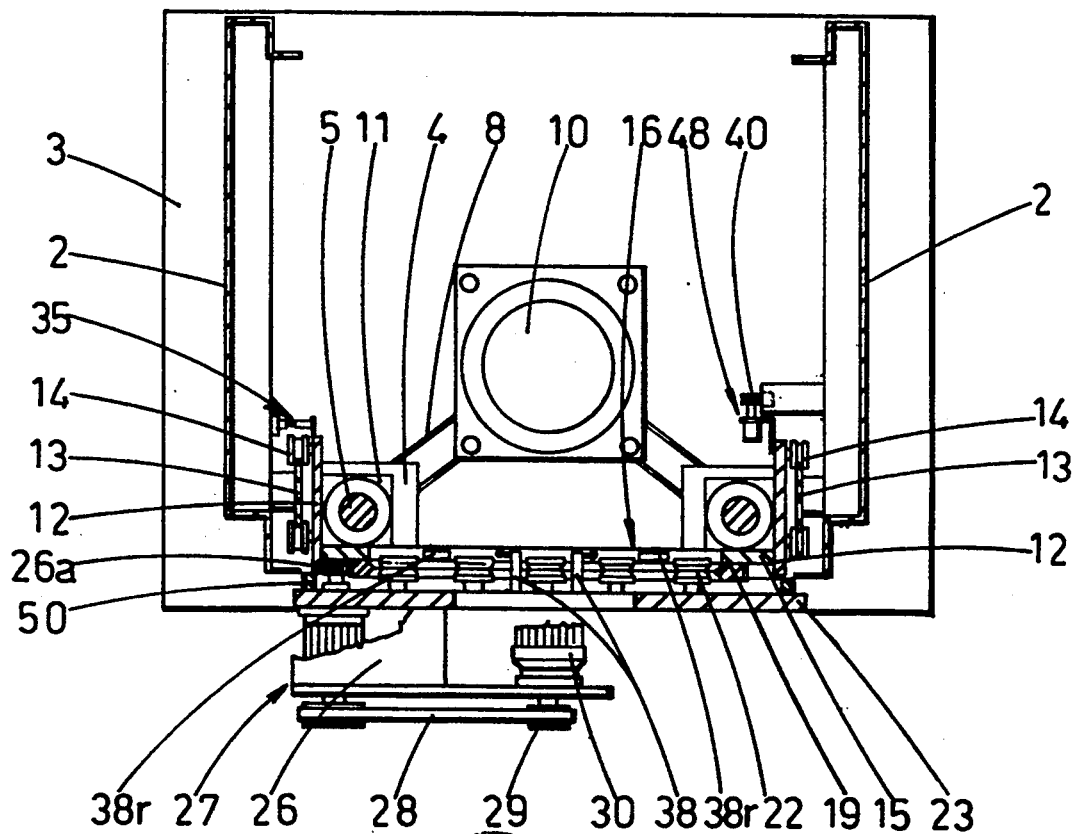
FIG. 3 shows a partially-sectioned plan view of the table of FIGS. 1 and 2 with some parts removed better to evidence others.

A crown wheel 19, fixed to the wall 15 by means of screws engaged in the holes 17, is coaxial to the circular aperture 16. The crown wheel 19 has an internal coaxial circular aperture 20 of a slightly smaller diameter than the circular aperture 16. The perimetral edge 21 of the circular aperture 20 is breasted by a plurality of horizontal-axis roller elements 22 (FIGS. 2 and 3), supported rotatably on a disc 23 and staggered one from another at regular angular intervals from the center of the disc 23. The disc 23 is coaxial to and arranged adjacently to a vertical face of the crown wheel 19, and is on the opposite side of the frontal wall 15 with respect to said crown wheel 19. The roller elements 22 and the perimetral edge 21 of the aperture 20 are shaped such as to enmesh in a way governed by the laws of rolling friction, such as to enable the disc 23 to rotate in both senses about the axis of the crown wheel 19 without its being able to translate axially with respect to it. The crown wheel 19 and the disc 23 will hereinafter together be referred to as support means of the patient rest plane 34.

A peripheral portion of the disc 23 is crossed by a hole 24 having its axis parallel to the axes of the roller elements 22 (FIG. 4): a pivot 25 is rotatably housed in the hole 24 and at one of its ends supports a cogwheel 26a engaging with the cogging of the crown wheel 19. The other end of the pivot 25 is engaged (not illustrated) in a portion of a support structure 26 solid to the disc 23: an epicyclic reduction gear 27 is keyed on to said other end of the pivot 25 and is driven (see FIG. 2) by a cogwheel 29 (with transmission by means of a cogbelt 28) keyed on the drive shaft of a bi-directional gear reducer 30 supported on the support structure 26.

A front face of the case 6 is defined by two bellows walls 32 and 33 arranged, in order, inferiorly and superiorly. An lower edge of the wall 32 is connected to a lower portion of the case 6, while an upper edge of the wall 33 is connected to an upper portion of the case 6. A top horizontal edge of the wall 32 is connected to a bottom edge of wall 15, while a bottom horizontal edge of the wall 33 is connected to a top horizontal edge of the wall 15. A patient rest plane 34 is connected (not illustrated) to a portion of the disc 23 arranged frontally to the case 6 (see FIG. 1 to identify the reciprocal positions of the disc 23 and the patient rest plane 34).

The gear reducer 30, the cogwheel 26a and the crown wheel 19 will hereinafter be referred to as the first movement means of the patient surface 34, while the gear reducer 10, the threaded bars 5 and the nuts 11 will be called second movement means of the patient rest plane 34.

Furthermore, the crown wheel 19 and the disc 23 will be called support means of the patient rest plane 34, permitting the patient rest surface 34 to rotate in both directions about their common horizontal axis and covering an angular distance of or above 180 degrees. A greater angular distance, say 270 degrees, is practicable when the invention is applied to an equipment and apparatus table.

The functioning of the examination table 1 will now be described.

To change the vertical height of the patient rest surface 34 it is sufficient to start the motor 10 in either direction according to the adjustment desired. Thus the bars 5 are set in rotation and the nuts 11 are raised or lowered, with a consequent vertical translation of the patient rest surface 34, which is connected to the nuts 11 by means of the disc 23, the crown wheel 19 and the wall 15. Obviously during the vertical translation of the patient rest surface 34 the bellows walls 32 and 33 stretch or contract and thus guarantee that the face 31 of the case 6 remains covered. Each threaded bar 5, together with a nut 11, constitutes a screw-nut coupling. To produce rotation in one sense or the other of the patient rest surface 34 about the disc 23 axis, the motor is started up, also in one direction or the other, so that the cogwheel 26a rolls on the cogging of the crown wheel 19 and therefore the entire support structure 26 and motor support on it rotate about the aperture 20 axis.

Two column 2 portions arranged inside the case 6, one portion at the inferior end and one at the superior end of the case 6, each support an endrun sensor, one lower 35 and one upper 36 (see FIG. 1). The endrun sensors 35 and 36 are of known type (for example: inductive, capacitative or alternatively simple contact microphones) and are able to sense the presence in their vicinity of a determined element, for example a nut 11, connected to and vertically mobile with the patient rest surface. When the sensors 35 and 36 read the presence of the determined element, they send a signal to a control switchboard 37 of known type, which stops the motor 10.

Figure 5:
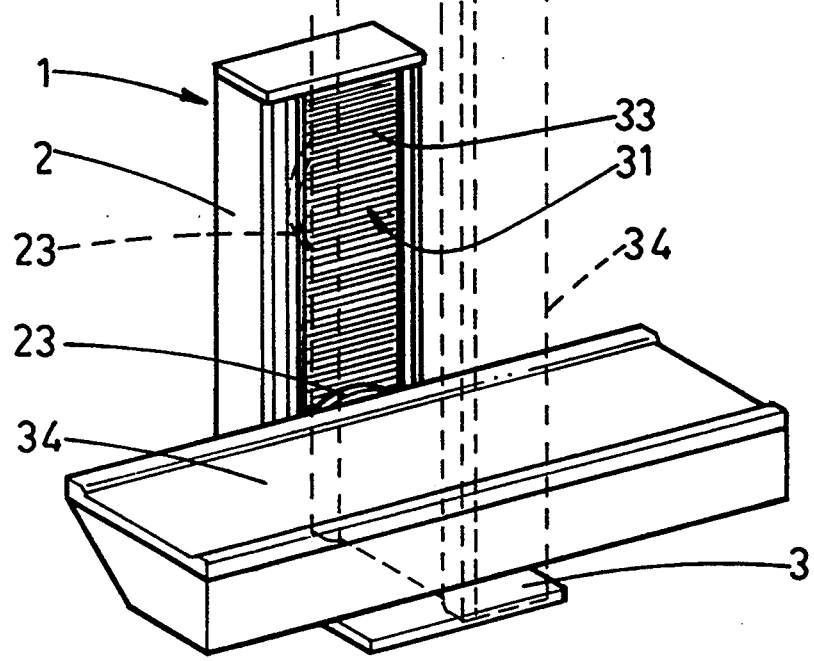
FIG. 5 shows a schematic perspective view of the relative mases of the examination table of the invention.

In a similar way other sensors 38 (again of known type, and similar to sensors 35 and 36) are supported to various zones of the disc 23 and can signal when they reach determined points of the perimetral edge 21 of the crown wheel 19, said points being identified by plates 38r solid to the wall 35. When this occurs, they send a signal to the control switchboard 37, which signal can be used to stop the motor 30 and/or to visualise the extent of the rotation the patient rest surface 34 about the crown wheel 19 with respect to an initial position. More precisely, the angular positioning between the limit values of plus or minus 90 degrees to the horizontal (as shown in FIGS. 1 and 5) is visualised on a monitor. A discontinuous line in FIG. 5 shows the maximum rotation position, i.e. vertical.

FIG. 4 shows that a sensor 48, preferably a potentiometer, is connected to one of the nuts 11.

The horizontal sensor exit pivot 49 bears a cogwheel 40 which is enmeshed with a vertical fixed rack 41 supported at the column 2 inside the case 6. While the patient rest surface 34 is vertically translating, the pivot 49 of the potentiometer 48 is caused to rotate about its own axis due to the the engagement of the cogwheel 40 and the rack 41, so that the potentiometer 48 can sense and display the moment-by-moment height of the patient rest surface: for this purpose the potentiometer 48 is inserted in a known-type digital visualising circuit (not illustrated) of the height of the patient rest surface 34. A similar sensor 58 performs the same task with regard to the rotation of the patient rest surface 34 about the horizontal axis X: this sensor 58 is enmeshed in the cogging of a disc 59 keyed on the disc 23 (see FIG. 1).

As has been shown, there is mechanical independence between vertical translation and rotation with respect to the horizontal plane X of the patient rest surface 34: this means that the patient rest surface 34 can be moved into any position, and can be raised or lowered and rotate at the same time.

What is claimed:

1. An apparatus for rotating and translating an examination table comprising:

support means for supporting the table:

first movement means coupled to the support means for rotating the table, at least 90 degrees in either direction, about a horizontal axis transverse to a longitudinal dimension of the table, the horizontal axis located at a substantially medial portion of the table; and second movement means coupled to the support means for vertically translating the support means and the table in the up and down directions.

2. An apparatus as in claim 1, wherein the second movement means is a rotatable threaded bar and a nut vertically translatable up and down the threaded bar, the nut coupled to the support means, the rotatable threaded bar rotatable by a first bi-directional motor.

3. An apparatus as in claim 1, wherein the support means comprises a crown wheel having an inner perimetral edge, the crown wheel fixedly coupled to the nut of the second movement means, and a disc rotatably coupled to the crown wheel and fixedly coupled to the table, wherein the first movement means comprises a cogwheel rotatably coupled to the disc and rotatably engagable with the crown wheel, the cogwheel rotatable by a second bi-directional motor, wherein rotation of the cogwheel by the second bi-directional motor rotates the disc and table, about the horizontal axis, in relation to the crown wheel.

4. An apparatus as in claim 1, further comprising first sensor means for sensing a vertical position of the table.

5. An apparatus as in claim 3, further comprising second sensor means for sensing an angular position of the table about the horizontal axis.

6. An apparatus as in claim 2, further comprising means for guiding the nut as the nut translates up and down the rotatable threaded bar.

7. An apparatus as in claim 6, wherein the means for guiding the nut comprises an idle roller pair coupled to the nut, and a vertical wall that engages and guides the idle roller pair coupled to the nut as the nut translates up and down the rotatable threaded bar.

8. An apparatus as in claim 7, wherein said second movement means further comprises a second rotatable threaded bar and nut for vertically translating a support means and table, wherein the crown wheel is coupled to the nut of the rotatable threaded bars, each nut having an idle roller pair that is engaged and guided by a corresponding vertical wall.

9. An apparatus as in claim 3, further comprising a plurality of roller elements rotatably coupled to the disc, wherein the roller elements enmesh with the inner perimetral edge of the crown wheel to rotatably couple the disc to the crown wheel.

* * * * *